United States Patent [19]

Ekenberg

[11] Patent Number: 5,693,784

[45] Date of Patent: *Dec. 2, 1997

[54] METHODS FOR CREATING AGGLOMERATES FROM COLLOIDAL PARTICLES

[75] Inventor: Steven J. Ekenberg, Mt. Horeb, Wis.

[73] Assignee: Promega Corporation, Madison, Wis.

[*] Notice: The portion of the term of this patent subsequent to Sep. 19, 2011, has been disclaimed.

[21] Appl. No.: 308,280

[22] Filed: Sep. 19, 1994

[51] Int. Cl.⁶ .............................. C12P 19/34; C07H 1/06
[52] U.S. Cl. .................. 536/25.4; 536/25.42; 435/91.1; 435/91.4
[58] Field of Search ..................... 536/25.4, 25.42; 435/91.1, 91.4

[56] References Cited

U.S. PATENT DOCUMENTS

| | | | |
|---|---|---|---|
| 3,700,555 | 10/1972 | Widmark et al. | 435/2 |
| 3,970,518 | 7/1976 | Giaever | 435/239 |
| 4,018,886 | 4/1977 | Giaever | 435/526 |
| 4,230,685 | 10/1980 | Senyei et al. | 435/526 |
| 4,267,234 | 5/1981 | Rembaum | 428/403 |
| 4,375,407 | 3/1983 | Kronick | 435/29 |
| 4,452,773 | 6/1984 | Molday | 435/1.37 |
| 4,508,625 | 4/1985 | Graham | 210/695 |
| 4,554,088 | 11/1985 | Whitehead et al. | 252/62.54 |
| 4,659,678 | 4/1987 | Forrest et al. | 436/512 |
| 4,710,472 | 12/1987 | Saur et al. | 435/308.1 |
| 4,738,773 | 4/1988 | Müller-Ruchholtz et al. | 435/29 |
| 4,795,698 | 1/1989 | Owen et al. | 435/4 |
| 4,978,610 | 12/1990 | Forrest et al. | 204/153.12 |
| 4,988,618 | 1/1991 | Li et al. | 435/6 |
| 5,108,933 | 4/1992 | Liberti et al. | 436/501 |
| 5,186,827 | 2/1993 | Liberti et al. | 210/222 |
| 5,200,084 | 4/1993 | Liberti et al. | 210/695 |
| 5,346,994 | 9/1994 | Chomczynski | 530/419 |
| 5,459,253 | 10/1995 | Wolin et al. | 536/25.42 |

FOREIGN PATENT DOCUMENTS 0 317 286 A2  5/1989  European Pat. Off. .

WO 90/10716  9/1990  WIPO .

OTHER PUBLICATIONS

Chirgwin et al., Biochemistry, 18(24): 5294–5299 1979.

Chomiczynski et al., Analytical Biochemistry, 162: 156–159 1987.

R. R. Oder, IEEE Trans. Magnetics, 12 (1976) 428–435.

C. Owen and P. Liberti, Cell Separation: Methods and Selected Applications, vol. 4, Pretlow and Pretlow eds., Academic Press, New York (1987).

Immunoassays for Clinical Chemistry, pp. 147–162, Hunter et al., eds., Churchill Livingston, Edinborough (1983).

L. S. Hersh and S. Yaverbaum, Clin. Chim. Acta, "Magnetic Solid-Phase Radioimmunoassay," 63, pp. 69–72 (1975).

J. T. Kemshead and J. Ugelstad, Molecular and Cellular Biochemistry, "Magnetic separation techniques: their application to medicine," 67, pp. 11–18 (1985).

Product Information Sheet, Magnetic Particle Concentrator, DYNAL MPC 1, Product No. 12001, DYNAL, A.S., Oslo, Norway, 1991.

Product Information Sheet, BioMag Separators, Product Nos. 4101S, 4102S, and 4106S, Advanced Magnetics, Inc., Cambridge, Massachusetts (1991).

Product Information Sheet, Magic™, magnetic immunochemistry method, Corning (1990).

Primary Examiner—Gary L. Kunz
Attorney, Agent, or Firm—Grady J. Frenchick; Stroud, Stroud, Willink, Thompson & Howard

[57] ABSTRACT

Methods for controllably creating agglomerates from particles of colloidal dimensions. Creation of agglomerates permits physical isolation or separation of, e.g., unwanted cell debris from cleared cell lysate comprising target particles, by the deposition or creation of a blocking or masking layer. Chaotropic agents are utilized to enhance colloidal particle agglomeration. The resulting agglomerant or "floc" can be deposited, as needed, in a separation/isolation process to create a blocking or masking layer on an "as needed" basis.

27 Claims, 1 Drawing Sheet

METHODS FOR CREATING AGGLOMERATES FROM COLLOIDAL PARTICLES

CROSS REFERENCE TO RELATED APPLICATION

Reference is made to commonly assigned, concurrently filed applications Ser. No. 08/308,561, filed Sep. 19, 1994, now U.S. Pat. No. 5,567,326 entitled "Multisample Magnetic Separation Device", and to Ser. No. 08/308,819, filed Sep. 19, 1994 entitled "High Efficiency Method For Isolating Target Substances Using a Multisample Separation Device", which applications are incorporated by reference herein in their entirety.

TECHNICAL FIELD

The present invention relates to processes for creating agglomerates, "flocs", or coagulants from particles of colloidal dimension or size. In one aspect, the present invention relates to methods or processes for separating or isolating target substances from other media. This invention is particularly applicable where small amounts of starting material (s) are to be processed. More specifically, the present invention relates to methods of separating or isolating a target substance or substances, or a complex from other media, especially where a multisample, preferably magnetic, separation device is utilized. Yet more specifically, this invention relates to methods for providing a physical separation or barrier layer between, e.g., a biological target substance or substances and interfering species, such as biological debris. In yet a further aspect, the present invention relates to the utilization of chaotropic species (i.e., chaos-forming species) to separate a colloidal suspension.

In a broader sense, aspects of this invention are applicable to any situation where a suspension or a solution of a target material is to be physically separated from an interfering substance or substances which can be collected or localized, e.g., by centrifugation. This invention provides the means by which the step of separating a target material from an interfering substance, e.g., by transfer of one away from the other via pipette or other means, can be completely avoided.

The concomitant of this invention is that where interfering substances can be localized, e.g., by centrifugation, subsequent processing of the target particles or target substance solution/suspension can be accomplished in the same centrifuge sample well.

BACKGROUND OF THE INVENTION

Colloidal particles are defined to be particles having a major dimension in the range of 1 millimicron to about 1 micron. Colloidal particles may be gaseous, liquid, or solid and occur in various types of suspensions. For example, colloidal particles may occur in solid-gas suspensions (aerosols), solid-solid suspensions, liquid-liquid suspensions (emulsions), and gas-liquid suspensions (foam). Generally speaking, colloidal particles have a surface area that is so large with respect to their volume that the particles do not settle out of the suspension by gravity. Further, the particles are small enough to pass through filter membranes. Macromolecules, i.e., proteins and other high polymers, are usually thought to be at the lower limit of the above range for particles of colloidal dimension. In terms of the present invention, "colloidal particles" is intended to include organic and inorganic particles of the indicated dimension.

Techniques for causing colloidal particles to come out of suspension have been found to be very useful in the separation or isolation of biological target substances from unwanted or interfering species. The present invention is a method of causing colloidal particles to come out of suspension under controlled conditions so as to create a physical barrier, layer, or "pill".

This invention solves a particular problem which sometimes occurs during the formation of biological complexes such as receptor/ligand complexes or in the separation of such receptor/ligand complexes from the medium in which they are dispersed. Specifically, it was found that, in the isolation of mRNA, after cell disruption or homogenation, dilution and centrifugation to generate cleared cell lysates, the precipitated proteins and cellular debris in the end of the centrifuge tube (usually in the form of a pellet) would interfere with complex formation between magnetic streptavidin particles and biotinylated oligo (dT):mRNA complexes. The specific interference caused by the unwanted proteins and cellular debris was interference in the release of mRNA from magnetic streptavidin particles upon addition of distilled water to collected streptavidin particles having biotinylated oligo (dT):mRNA complexes thereon. This invention solves the above problem.

However, this invention is broadly applicable to any circumstance where a target substance is to be isolated from a medium and physical separation from interfering materials is desired. In the context of a biological target substance, this invention provides enhanced reproducibility, even where small or very small samples are involved, by reducing sample loss. A specific, preferred application of this invention where a multiple well plate is used in a magnetic separation process is that described in applicants' commonly assigned and concurrently filed patent application referred to above.

SUMMARY OF THE INVENTION

Briefly, in one aspect, the present invention is a method of agglomerating colloidal particles in an aqueous medium utilizing a chaotropic species or chaotropic agent. The present method includes the steps of first providing a quantity of particles of colloidal dimension in an aqueous medium.

Next, a chaotropic agent, e.g., guanidine thiocyanate (GTC) extraction buffer and a dilution buffer are provided. The dilution buffer preferably comprises tris-HCl, SSC (i.e., sodium chloride/sodium citrate buffer), sodium dodecyl sulfate, and EDTA. The GTC buffer, the dilution buffer, and the colloidal particles are mixed, causing the colloidal particles to agglomerate or accumulate into substantially larger particles or agglomerates. The substantially larger particles are no longer of colloidal dimension and can be centrifuged into a layer with ease. Generally speaking, the GTC extraction buffer comprises guanidine thiocyanate (4M), sodium citrate (0.025M), and 2% beta-mercaptoethanol (BME).

In a related aspect, the present invention is a method for isolating or detecting (or both) a target substance of biological interest from interfering biological debris, especially where a multi-well separation device is employed. Biological target substances in the present invention are collected by the formation of a complex with a second substance, the complex having properties which permit it to be separated from the medium in which it is dispersed by application of an external influence such as electric field, magnetic field, U.V., visible or infrared radiation or temperature change. "Chaotropic species" or "chaotropic" agents, as those terms are used herein, are to be broadly construed to mean any chaos-forming or chaos-enhancing entities. Without being limited to a theory, chaotropic agents are believed to act by interfering with the hydrogen bond structure of regular water.

Destruction of water structure decreases what is known as hydrophobic effect which tends to promote the unfolding and possible dissociation of, e.g., protein molecules.

As applicable to the present invention, the chaotropic agent reduces the normally ordered water structure and thereby permits the colloidal particles to approach each other more closely. During closer approach, the colloidal particles tend to collect or agglomerate, i.e., to come out of suspension. When this happens, the particle collection achieves a larger size and can be controllably deposited, e.g., by centrifugation or filtration to create a physical barrier in a separation/isolation process.

Chaotropic salts are salts of chaotropic ions. The salts are highly soluble in aqueous solutions. The chaotropic ions provided by such salts, at sufficiently high concentration in aqueous solutions of proteins or nucleic acids, cause proteins to unfold, nucleic acids to lose secondary structure or, in the case of double-stranded nucleic acids, to melt (i.e., strand-separate). Chaotropic ions include guanidinium, iodide, perchlorate and trichloroacetate. Preferred in the present invention is the guanidinium ion. Chaotropic salts include guanidinium chloride, guanidinium thiocyanate (which is sometimes referred to as guanidinium isothiocyanate), sodium iodide, sodium perchlorate, and sodium trichloroacetate. Preferred are the guanidinium salts.

With any chaotropic agent or salt used in the invention, it is desirable that the concentration of the salt, in any of the solutions in which the salt is employed in carrying out the invention, remain below the solubility of the salt in the solution under all of the conditions to which the solution is subjected in carrying out the invention.

In a preferred practice of the present invention, the target substance interacts with a magnetically responsive second particle to form a complex which may be separated from the biologic medium by application of magnetic separation techniques. While this invention is specifically disclosed with reference to magnetic separation techniques, other techniques such as application of electrical energy, e.g., repulsion/attraction, irradiation, or chemical interaction and the like, may be employed.

As used herein, the term "target substance" or "target particle" refers to any member of a specific binding pair, i.e., a pair of substances or a substance and a structure exhibiting a mutual affinity of interaction and includes such things as cell components, biospecific ligands and receptors.

"Ligand" is used herein to refer to substances, such as biotin, antigens, haptens, proteins, nucleic acids and various cell-associated structures, having at least one characteristic determinant or epitope, which are capable of being biospecifically recognized by and bound to a receptor.

"Receptor" is used herein to refer to any substance or group of substances having a biospecific binding affinity for a given ligand, to the substantial exclusion of other substances. Among the receptors determinable via biospecific affinity reactions are biotin-binding proteins (e.g., avidin and streptavidin), antibodies (both polyclonal and monoclonal), antibody fragments, enzymes, proteins, nucleic acids, and the like. The determination of any member of a biospecific binding pair is dependent upon its selective interaction with the other member of the pair.

As used herein, the term "magnetic" is meant to refer to permanently and temporarily magnetic materials, and to magnetically responsive materials, i.e., materials capable of being magnetized in the presence of a magnetic field but which are not themselves magnetic in the absence of such a field, such as paramagnetic materials.

DETAILED DESCRIPTION

Figure 1:
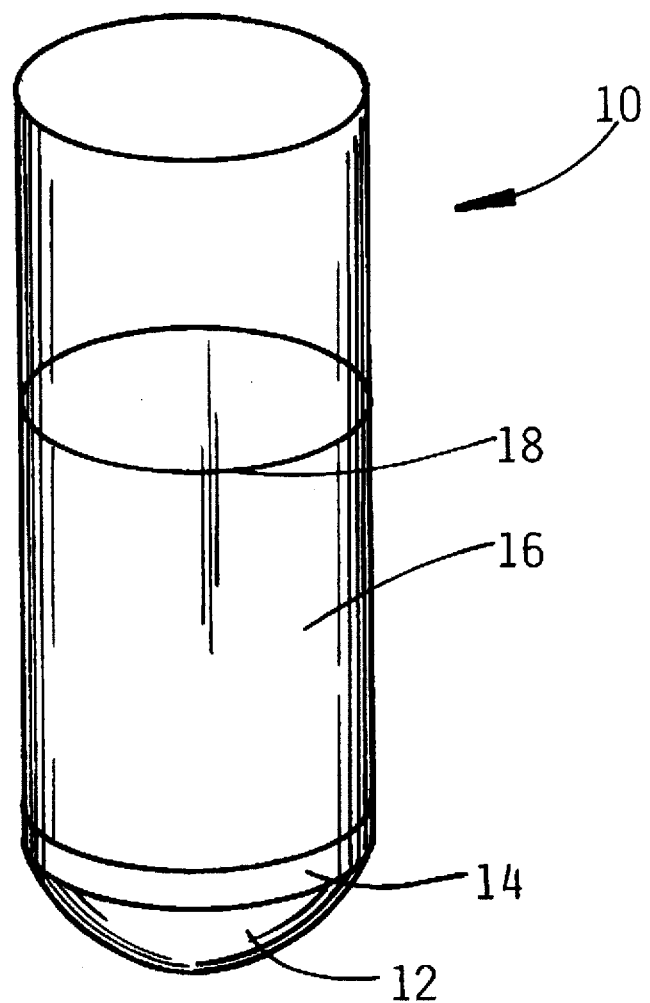
FIG. 1 is a perspective schematic illustration of a microcentrifuge tube or well utilizing the present invention.

As is described above, this invention is preferably utilized with magnetic separation devices for separation of magnetic particles from nonmagnetic media utilizing a multi-well or multi-titer separation device. While a 96-well separation device is disclosed, a separator with five or more wells can be used more effectively in a practice of this invention. The present invention is particularly well-suited for use in separating biological substances of interest in various laboratory and clinical procedures involving biospecific affinity reactions. Accordingly, the present invention will now be described in detail with respect to such endeavors. However, those skilled in the art will appreciate that such a description of the invention is meant to be exemplary only and should not be viewed as limitative of the full scope thereof.

A preferred method in accordance with the present invention utilizes particles which are magnetically responsive and which comprise a receptor capable of binding the substance of interest in the test sample. After the receptor binds the target substance, a magnetic separator can be used to remove the magnetic particles bound to the substance of interest from the test medium.

Biospecific affinity reactions may be employed in testing biological samples for the determination of a wide range of target substances. Representative target substances include cells, cell components, cell subpopulations (both eucaryotic and procaryotic), bacteria, parasites, antigens, proteins, specific antibodies, specific biological factors, such as vitamins, viruses and specific nucleic acid sequences, e.g., mRNA. Thus, the magnetic separation aspect of this invention has application in cell separations for the analysis or isolation of cells including, by way of example: T-cells from a T-cell lymphoma cell line; B-cells from a B-cell lymphoma cell line; CD4 positive cells from leukocytes; and lymphocytes from leukocytes.

The methods in accordance with the invention may also be used for immunospecific isolation of monocytes, granulocytes and other cell types; removal of rare cells; depletion of natural killer cells; determination of reticulocytes; and assays for neutrophil function, e.g., for determining changes in membrane potential, performing oxidative burst analysis, phagocytosis assays and opsonization studies.

Similarly, the magnetic separation aspect of the present method may be used in separation of pathogens, including but not limited to the separation of various bacteria and parasites from fecal matter, urine, sludges, slurries and water (e.g., ground water or streams). The present invention may also be used in separating various bacteria in food products (liquids to solids), sputum, blood, urine, body fluids, and homogenates of body fluids.

Magnetic particles may comprise paramagnetic materials such as, for example, metals (e.g., iron, nickel or cobalt), metal alloys (e.g., magnetic alloys of aluminum, nickel and cobalt) and metal oxides (e.g., $Fe_3O_4$ or $Fe_2O_3$). The preferred material is the paramagnetic ferric oxide.

The paramagnetic particles may be provided with a nonmagnetic polymeric matrix or coating. Suitable materials are composed of a crystalline core of magnetically responsive material surrounded by molecules which may be physically absorbed or covalently attached to the magnetic core. For example, preferred are particles of an iron oxide core surrounded by receptor molecules or molecular probes depending on the type of ligand to be separated.

The preferred magnetic particles for use in carrying out this invention are particles having a size in the range of about 500 nm to about 2 μm, i.e., noncolloidal particles that are subject to settling if undisturbed. Magnetic particles having the above-described properties are, for example, streptavidin-coated iron oxide paramagnetic particles which are commercially available from Promega Corporation, Madison, Wis., U.S.A. under the trade designation Streptavidin MagneSphere® Paramagnetic Particles. Streptavidin MagneSphere® Paramagnetic Particles (SA-PMP's) are used in the magnetic separation or purification of various biotinylated molecules. Conversely, streptavidin may be separately purchased, e.g., from Promega Corporation, and coated upon paramagnetic particles, e.g., those particles available from Advanced Magnetics, Cambridge, Mass., U.S.A. In the context of this invention, mRNA may be isolated/separated.

For cell separations, the test medium is typically prepared from body fluids or tissues, such as blood, urine, sputum, secretions, or tissue samples. If magnetic separation is to be utilized, it is preferable to add the magnetic particles to the test medium in a buffer solution. A preferred buffer solution for, e.g., RNA isolations, is PolyATtract guanidine thiocyanate (GTC) Extraction Buffer containing β-mercaptoethanol commercially available from Promega Corporation, Madison, Wis., U.S.A. The buffer solution should be isotonic, with a pH of about 7. The target substance may be added to the test medium before, after or simultaneously with introduction of the blocking particles. However, for hybridization assays, e.g., mRNA purification, it has been found that the magnetic particles are suitably added to the target substance after the hybridization reaction occurs and after blocking or masking of the cellular debris, according to one aspect of this invention. The test medium is usually incubated to promote binding between the receptor and any ligand of interest present therein. Incubation is typically conducted at room temperature, at a temperature slightly above the freezing point of the test medium (i.e., 4° C. ) or even at elevated temperatures (e.g., 70° C.). The period of incubation is normally of short duration (i.e., about 1 to about 15 minutes). The test medium may be agitated or stirred during the incubation period to facilitate contact between receptor and ligand.

After binding of the receptor to the substance of interest is allowed to occur, magnetic separation of the magnetic particles from the test medium is performed in accordance with the above-cited co-pending application.

One of the advantages of the present invention is that, in one practice, a target substance such as mRNA, can be hybridized in solution to the biotinylated oligo (dT) probe, rather than to a probe directly coupled to paramagnetic particles. This permits the user to achieve the combined speed and efficiency of solution hybridization with the convenience and speed of magnetic separation. The Streptavidin Paramagnetic Particles, SA-PMP (especially the MagneSphere® particles available from Promega Corporation), exhibit a high binding capacity for biotinylated oligonucleotides and very low nonspecific binding of nucleic acids. While the binding capacity of the SA-PMP varies with the specific oligonucleotide probe used for biotinylated oligo (dT), the binding capacity is approximately 1 nmol of free probe captured per mg of SA-PMPs.

The method of this invention utilizes "blocking" or "masking" particles to reduce or eliminate interference in the formation of magnetic complexes by cellular debris and precipitated proteins. The preferred blocking particles used in this invention are carboxylated polystyrene latex (especially fluorescent labeled yellow versions), 0.043 μm particles, commercially available from Magsphere, Inc. of Pasadena, Calif., U.S.A. The blocking particles are added in sufficient quantity so as to cover, layer over, encase, encapsulate, or create a barrier over cellular debris which tends to be located in the extreme end of a centrifuge tube following centrifugation. The blocking particles generally are used in the isolation process between the steps of homogenation of the biological source containing the target particles and centrifugation of the homogenized medium to generate cleared lysate containing target particles.

In other words, blocking or masking particles are utilized in the isolation method after hybridization of mRNA and biotinylated oligo (dT) probe and before a biospecific affinity reaction is run. In the above-described, preferred description of the invention, after the above steps, SA-PMPs are added to the cleared lysate to generate a magnetically-responsive complex with the mRNA target particles which can then be magnetically isolated.

The use of multi-well, magnetic separation techniques suggests several of the criteria which must be considered when selecting blocking or masking particles for utilization of this invention where other, non-magnetic, separation techniques are to be employed.

Of primary importance, the blocking or masking particles chosen should not, themselves, interfere with intended complex formation. In the context of the preferred practice of this invention, carboxylated 0.04 μm polystyrene particles do not interfere with complex formation between mRNA target particles and paramagnetic streptavidin particles. If other target particle/ligand interactions, e.g., chemical bonding, hydrogen bonding, electro-repulsion, irradiation, electro-attraction, physical restraint (e.g., molecular sieve), are used to create complexes, the blocking particles selected must not interfere with that complex formation.

Also to be considered is that the blocking or masking particles chosen should be of a size, density, chemical composition, or surface configuration or chemical characteristics so that they will agglomerate, accumulate or otherwise associate to form a protective layer or coat over unwanted, interfering debris in, e.g., a centrifugation step. In this manner, interference with complex formation is minimized or eliminated because a physical separator, or a barrier layer between the debris (i.e., cell lysate solids) and cleared lysate or medium containing target particles is provided. The preferred blocking particles, under the conditions described below, have been found to increase substantially in apparent volume. This feature tends to make them particularly attractive for utilization in the present invention.

Further, the masking or blocking particles should interact with each other in a compacting, aggregating, or associating manner, e.g., in response to the gravitational forces generated during centrifugation, to create a layer, encasing, or coating which is substantially impermeable to the contained or "trapped" interfering debris. It is the trapping or localization of potentially interfering debris by utilization of blocking particles which provides the many advantages of this invention discussed above.

The utilization of masking or blocking particles provides a further unexpected advantage which is particularly applicable to multi-well separation systems, especially if automated systems are contemplated. The quantity of blocking particles can be used to adjust the volume relationship between cleared lysate and debris generated in centrifugation. Since the particles occupy part of the volume, e.g., of a Microtiter™ well (Microtiter is a trademark of Dynal, Inc., Lake Success, N.Y., U.S.A), their quantity may be adjusted to control precisely liquid levels within each well. In one application of this invention, the volume of colloidal particles added to the system during the isolation process is substantially less than volume of agglomerate produced therefrom. This results in amplification of the colloid particles volume, thereby enhancing the utility of this invention for use in liquid level adjustment.

In other words, in an aspect of this invention, liquid levels within an individual well can be controlled without the need to change the quantity of potentially scarce biological starting material containing target particles. Where magnetic pin separators which are dipped into an array of wells are used (e.g., those described in the concurrently filed application incorporated by reference above), the ability to control liquid levels within the system, in a cost-effective manner, may be very useful.

One skilled in this art will be able to select appropriate blocking particles or materials in light of the above teaching and of the isolation process employed. Substantially chemically inert, non-magnetic, colloidal, polyolefinic particles of the above-discussed size to work well if magnetic separation is employed. Other classes of particles could include ceramic materials, molecular sieves, carbon particles, electrically conductive or non-conductive particles of all chemistries, polymeric or polymerizable particles of other types, latexes, diatomaceous earth, non-soluble powders, glycerol, polyethylene glycol polyethers (PEG), acrylamide particles, agaroses, and the like.

The following examples further describe in detail the manner and process of making and using the present invention. The examples are to be considered as illustrative but not as limiting of this invention. All temperatures given in the examples are in degrees Celsius, unless otherwise indicated.

EXAMPLE 1

As is noted above, the present invention is particularly applicable to situations where a multiple well magnetic separation device is employed. For example, mRNA can be isolated in parallel from 48, 96 (or more) tissue or cell samples and converted into first strand cDNA in approximately 2.5 hours (excluding sample preparation). A separator having a well array of five or more wells is generally what is intended by the terminology of "multiple well" as used herein. Polymerase chain reaction (PCR) processes may be performed on the cDNA in the same time period with no further sample preparation.

In this example of the present invention, high capacity streptavidin paramagnetic particles (SA-PMP), biotinylated oligo (dT), a 96 pin magnetic separator, and non-magnetic blocking particles were employed. First strand cDNA then was synthesized by the simple addition of M-MLV (H–) Reverse Transcriptase reaction mixture directly to the multiple well plate. The cDNA thereby generated was generally more stable than RNA and can be directly stored in the 96 well plate. Because an entire mRNA population is represented in each sample, the cDNA can be probed for multiple genes from the same tissue or cell sample. Further, by utilization of a multiple well microtiter plate, samples may be processed in parallel, thereby facilitating direct comparison between identical samples exposed to differing process conditions.

A typical kit for practicing the present invention with, e.g., a 96 well plate magnetic separation device, has the following components:

30,000 u M-MLV (H–) Reverse Transcriptase, 200 u/µl 3 ml RT 9600 Gold Buffer

50 µl dNTP Mix, 10 mM of each dNTP

175 µg Oligo(dT)$_{15}$ Primer, 500 µg/ml 10,000 u rRNasin® Ribonuclease Inhibitor, 40 u/µl 80 µl Mouse Liver Lysate, 125 µg/µl The above-listed components are sometimes referred to as the cDNA Master Mix.

120 ml PolyATtract® GTC Extraction Buffer 15 ml Hybridization Buffer with Biotinylated Oligo(dT) Probe 15 ml Blocking Particles, 0.04 micron carboxylated, yellow dyed, polystyrene particles 20 ml Streptavidin MagneSphere® Paramagnetic Particles available from Promega Corporation 150 ml PolyATtract Wash Solution [SSC, 0.5×Solution]

25 ml Nuclease-Free Water 6 96 Well V-Bottom Plates 6 48 Well GeNunc™ Modules

2 GeNunc™ Frames

2 GeNunc™ Frame Supports

3 Plate Sealers

24 Strip-Ease® PCR Tube Caps

The above materials are available from Promega Corporation, Madison, Wis., U.S.A.

GeNunc frames and frame supports are commercially available from the Nunc Inc. located in Naperville, Ill., U.S.A. Strip-ease PCR tube caps are commercially available from the Robbins Scientific Corporation located in Sunnyvale, Calif., U.S.A.

Utilizing the above components, the following steps were performed:

1. GTC extraction buffer was added to tissue, e.g., mouse liver lysate, at a ratio of 20 µl per 2.5 mg (or less) of tissue or 20 µl per 1×10$^5$ (or less) tissue culture cells.

2. The mixture of step 1 was homogenized using a Polytron Homogenizer, Brinkmann Instruments, Westbury, N.Y.

3. 20 µl of each sample was transferred to a well. For example, 96 such 20 µl samples are transferred in a typical application of the present invention.

4. 40 µl of prewarmed (e.g., to 70° C.) hybridization buffer comprising biotinylated oligo (dT) probe was added per well and incubated at room temperature for five minutes.

5. 35 µl of blocking or masking particles were added per well, the plate was sealed, and centrifuged for ten minutes at room temperature. The centrifugation step should be accomplished at approximately 1,700×g. This centrifugation step traps precipitated proteins and insoluble cell material underneath the pellet of blocking particles.

At this point, a typical sample will contain (proceeding from the bottom of the centrifuge tube) a pellet or collection of cell debris covered by a pellet or layer of masking or blocking particles. Lastly, above the pellet of blocking particles is cleared cell lysate comprising mRNA target particles dispersed in the medium, i.e., buffer.

Referring now to FIG. 1, shown in expanded perspective view, is one titer well 10 of what would be an extended array, e.g., 96, of such wells. Well 10 appears as it would subsequent to centrifugation step 5 above. Within well 10 is cell debris and precipitated proteins in the form of a pellet 12. Covering pellet 12 is a layer of blocking particles 14. Over layer 14 is cleared cell lysate 16. Cleared cell lysate 16 contains mRNA which, in further processing, will be separated from the buffer medium. Blocking particle layer 14 comprises 0.04 micron carboxylated polystyrene particles (i.e., a latex). A sufficient quantity of such particles is added to create layer 14 which separates cleared cell lysate 16 from cell debris 12. Prior to the present invention, in order to prevent interference between cell debris 12 and a target substance in lysate 16, it would have been necessary for cleared lysate 16 to be removed from cell 10 to a clean reaction chamber. It is elimination of this procedure which is one of the primary advantages of the present invention. Lysate 16 protected from debris 12 by layer 14 may now be exposed to subsequent processing steps, e.g., magnetic separation, resulting in the collection of target substance, e.g., mRNA, therefrom.

Further, the width of layer 14 may be adjusted by changing the quantity of particles 14, thereby changing liquid level 18 (assuming a fixed quantity of liquid). The ability to adjust liquid level 18 by adjusting the quantity of blocking particles 14 is potentially a useful tool for automating isolation/transcription/amplification processes.

6. 60 µl of SA-PMPs were added to each well and incubated at room temperature for two minutes.

EXAMPLE 2

The pin array of a magnetic separator described in the above-cited concurrently filed application was treated in 0.5 m sodium hydroxide for one minute before use. The pins were then rinsed with sterile $H_2O$.

EXAMPLE 3 mRNA Purification

The array of wells generated in Example 1 was then placed into the base of a multiple pin/magnetic separator as described in the above-referenced, concurrently filed application. The hinges of the pin plate were positioned in the hinge channels of the base and the pin plate was carefully lowered into the Microtiter™ plate. The external magnet pack was then placed on the pin plate, contacting the pin ends and the admixtures were incubated until the magnetic particles were cleared from the lysate, typically about 90 sec.

The pin plate and magnet were then raised to a 45° angle, and the Microtiter™ plate containing the cell lysates was replaced with a fresh plate containing 155 µl of 0.5×SSC 10 µg/ml BSA in each well. The magnet pack was removed and the attached particles were released to wash by raising and lowering the pin plate. The particles were recaptured by placing the magnet pack in contact with the pins. The release and recapture steps were repeated for a total of two washes of the SA-PMP complexes. The rinse Microtiter™ plate was then removed and replaced with a GeNunc plate containing 20 µl of $dH_2O$ in each well. The pin plate and magnet were lowered so that the pins were immersed. The magnet was removed and the particles were released in nuclease free water and recaptured, releasing the mRNA into solution. After 1 min, the magnet was returned to position atop the pin plate and collected the particles on the pins, typically about 90 sec. The remaining water medium contained purified mRNA.

EXAMPLE 4

The purified isolated mRNA generated in Example 3 was used to synthesize cDNA by adding 10 µl Reverse Transcriptase Master Mix, components commercially available from Promega Corporation, Madison, Wis., U.S.A., to the wells and incubating the mixture at 37° C. for 30 minutes followed by heat inactivation for 5 minutes at 95° C.

In summary, the present invention provides a simple, cost-effective, efficient, high throughput method for effective separation of multiple small samples and facilitating processing steps, especially the magnetic particle-ligand complex.

EXAMPLE 5

In this example, carboxylated polystyrene latex blocking particles colored with fluorescent yellow dye were used. Such particles are commercially available from Magsphere Inc., Pasadena, Calif., U.S.A. The particles had a size of about 0.043 µm and comprise a yellow color water-based latex with about 10% dyed polymer particles in water medium on a weight per unit volume basis. The yellow color is used primarily to identify the presence of the particles during the processing steps.

Aggressive centrifugation of the water-based latex blocking particles, substantially as purchased, produced no precipitate or agglomerate. Under observation in a micro fluoroscope, the substantially independent particles appear to float in the aqueous medium, apparently being subject to Brownian movement.

The blocking particles have been found to create agglomerates, aggregates, clusters, or "flocs" which are capable of centrifugation, as follows:

Two ml of stock carboxylated polystyrene latex particles were placed in a centrifuge tube. Six ml of GTC Extraction Buffer was added to the tube and next, 12 ml of dilution buffer which has been heated to 70 degrees C. GTC extraction buffer is commercially available from Promega Corporation under the trade name PolyATtract® and comprises: 4M guanidine thiocyanate, 25 mM sodium citrate, and 2% β-mercaptoethanol. The dilution buffer comprises 0.01M TrisHCl, pH 7.5, 6×SSC, 0.24% sodium dodecyl sulfate (SDS), 0.001M EDTA, and 1% beta-mercaptoethanol (BME). The materials are mixed and centrifuged at 1,700×G for ten minutes. Under fluorescent microscopy, the resulting agglomerates are sheetlike. The particles did not evidence Brownian motion. Even though only about 2 ml of particles was employed in the process, their packed volume after agglomeration and centrifugation is approximately 5 ml.

EXAMPLE 6

In this example, spherically-shaped agglomerates or coagulants were created.

GTC extraction buffer and dilution buffer, in the amounts indicated in Example 5, were first mixed together. Two ml of stock masking particles were then added to the premixed buffers. After mixing and centrifuging the mixture, as described in Example 5, the agglomerates appeared to be substantially spherical under fluorescence microscopy.

EXAMPLE 7

Individual mixtures of 2 ml of stock particles and the quantities of Tris, SDS solution, 6×SSC solution and EDTA solution indicated in Example 5 were prepared. After mixing and centrifugation under the conditions indicated in Example 5, no agglomerates or precipitate was generated. From this it was concluded that all the above buffer components had to be present for the desired agglomeration reaction to occur.

EXAMPLE 8

This example involves the collection by agglomeration of colloidal-dimension magnetic particles that could not otherwise be collected using conventional, low magnetic strength separation techniques.

In this example, magnetically responsive particles of less than one micron major diameter would be used. Particles to which this aspect of the invention applies are described in U.S. Pat. No. 4,795,698 to Owen et al. (referenced description also cited in U.S. Pat. No. 5,200,084 to Liberti et al., at column 2, lines 65–68), and in U.S. Pat. No. 5,108,933 (referenced description cited as U.S. patent application Ser. No. 389,697 filed Aug. 4, 1989, in the '084 Liberti et al. patent column 3, lines 35 to 41). Both the above patents are incorporated by reference herein. Magnetically responsive particles of that dimension would be of true colloidal dimension and would not be removed from solution or suspension by conventional centrifugation. In this example, submicron magnetically responsive particles would be mixed with GTC buffer, and dilution buffer in ratios substantially as disclosed in Example 5. Agglomeration is permitted to occur generating particles of a supra micron (i.e., above 1 micron), non-colloidal major dimension. These substantially larger particles may be separated from the medium in which they were dispersed by centrifugation or by application of relatively low magnetic fields.

EXAMPLE 9

The compositions of buffers and solutions referred to herein are as follows:

1 X PBS, pH 7.4:
  0.2 g/L KCl
  8.0 g/L NaCL
  0.2 g/L $KH_2PO_4$
  1.15 g/L $Na_2HPO_4$

PolyATtract® GTC Extraction Buffer:
  4M guanidine thiocyanate
  25 mM sodium citrate
  2% β-mercaptoethanol PolyATtract® Wash Solution:
  7.5 mM sodium citrate
  75 mM NaCl
  10 µg/ml bovine serum albumin (BSA)

Hybridization Buffer with Biotinylated Oligo(dT) Probe:
  10 mM Tris-HCl, pH 7.1
  90 mM sodium citrate
  900 mM NaCl
  1 mM EDTA
  0.25% SDS
  1% β-mercaptoethanol
  75 nM Biotinylated Oligo(dT) Probe RT 9600 Gold Buffer:
  40 mM Tris-HCl, pH 8.3
  202 mM KCl
  6 mM $MgCl_2$
  8 mM DTT
  2.7% yellow dye 20×SCC:
  3.0M sodium chloride
  0.3M sodium citrate
  pH adjusted to 7.0 with NaOH.

EXAMPLE 10

Messenger RNA, purified from 2-fold serially diluted Mouse Liver Lysate, as described above, was reverse transcribed and amplified by PCR for detection of a rare cytokine mRNA, IL-1β. Amplification was performed using Taq DNA Polymerase from Boehringer Mannheim according to their specifications for PCR conditions. Five microliters of each 30 µl cDNA sample were amplified in a 50 µl PCR reaction containing 1µM of each primer. Twenty microliters of each PCR reaction were analyzed on a 2% agarose gel and stained with ethidium bromide. Each 20 µl sample corresponds to 1/15 of the original tissue or cell sample. RT-PCR product was faintly detected at the lowest level of starting material.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

What is claimed is as follows:

1. A method of agglomerating colloidal particles in an aqueous medium, the method comprising the steps of:
   providing a quantity of particles of colloidal dimension in an aqueous medium;
   providing a GTC buffer;
   providing a dilution buffer;
   mixing the GTC buffer, the dilution buffer and the colloidal particles to cause the colloidal particles to agglomerate into particles substantially larger than particles of colloidal dimension and which can form a barrier of the agglomerates in the medium.

2. A method according to claim 1 wherein the colloidal particles have a major dimension in the range of about 1 millimicron to about 1 micron.

3. A method according to claim 1 wherein the GTC buffer and the dilution buffer are first mixed together, and the colloidal particles are thereafter added and mixed with the buffer mixture resulting in the production of agglomerates.

4. A method according to claim 1, wherein the GTC buffer, the dilution buffer, and the colloidal particles are mixed in the presence of cell lysate which is relatively denser than said particles, wherein the cell lysate includes biological debris, and wherein a barrier of agglomerates is formed over the biological debris by centrifugation.

5. A method according to claim 4 wherein the cell lysate is generated in a process of purifying detection of biological target molecules selected from the group consisting of DNA, RNA or proteins.

6. A method according to claim 1 wherein the GTC buffer is mixed with the colloidal particles and the dilution buffer is thereafter added to create the agglomerates.

7. A method according to claim 1, wherein the agglomerates have a major dimension of at least one micron.

8. A method according to claim 1, wherein colloidal particles having a major dimension of less than 1 micron are used, and wherein the method further includes the step of performing an immunoassay.

9. A method according to claim 1 wherein the GTC buffer comprises guanidine thiocyanate, sodium citrate, and beta-mercaptoethanol.

10. A method according to claim 1 wherein the dilution buffer comprises tris-HCl, sodium dodecyl sulfate, SSC, and EDTA.

11. A method of agglomerating colloidal particles in an aqueous medium, the method of comprising the steps of:

providing a quantity of particles of colloidal dimension in an aqueous medium;

providing a chaotropic agent;

mixing the chaotropic agent and the colloidal particles to cause the colloidal particles to agglomerate into particles substantially larger than particles of colloidal dimension and which can form a barrier of the agglomerates in the medium.

12. A method according to claim 11 wherein the colloidal particles have a major dimension in the range of about 1 millimicron to about 1 micron.

13. A method according to claim 11 wherein the chaotropic agent comprises a GTC buffer and a dilution buffer.

14. A method according to claim 13, wherein the GTC buffer, the dilution buffer, and the colloidal particles are mixed in the presence of cell lysate which is relatively denser than said particles, wherein the lysate includes biological debris, wherein agglomeration is allowed to occur, and wherein a barrier of the agglomerates is formed over the biological debris by centrifugation.

15. A method according to claim 14 wherein the cell lysate is generated in a process of purifying detection of biological target molecules selected from the group consisting of DNA, RNA or proteins.

16. A method according to claim 11 wherein the GTC buffer is mixed with the colloidal particles and the dilution buffer is thereafter added to create the agglomerates.

17. A method according to claim 11, wherein the agglomerates have a major dimension of at least one micron.

18. A method of isolating a nucleic acid target substance from biological debris in an aqueous medium, the method comprising the steps of:

adding a ligand material to the aqueous medium, to form a target-ligand complex;

adding to the medium particles of colloidal dimension and a chaotropic agent;

mixing the chaotropic agent and the colloidal particles causing the colloidal particles to agglomerate into particles substantially larger than particles of colloidal dimension;

forming a barrier of the agglomerates over the debris particles by centrifuging the medium;

adding magnetic particles to the medium, the magnetic particles including receptors capable of binding the target-ligand complex;

hybridizing the magnetic particles to the target-ligand complex to form a target-ligand-particle complex; and applying magnetic force to the medium to isolate the target-ligand-particle complex from the biological debris.

19. A method of claim 18, wherein the chaotropic agent comprises a GTC buffer and a dilution buffer.

20. A method of claim 19, wherein the dilution buffer comprises tris-HCL, sodium dodecyl sulfate, SSC, and EDTA.

21. A method of claim 18, wherein the isotonic buffer present during magnetic particle addition is a guanidine thiocyanate extraction buffer containing β-mercaptoethanol.

22. A method of claim 12, wherein the nucleic acid target substance is mRNA.

23. A method of claim 22, wherein the ligand is a biotinylated oligo (dT) probe, and the receptor of the magnetic particles is streptavidin.

24. A method of claim 18, wherein the magnetic particles are paramagnetic.

25. A method of claim 18, wherein the colloidal particles added to the medium have a major dimension in the range between about 1 millimicron to about 1 micron.

26. A method of claim 25, wherein the colloidal particles added are carboxylated polystyrene latex particles.

27. A method of claim 18, wherein the isotonic buffer is added to the medium before agglomeration comprises guanidine thiocyanate, sodium citrate, and beta-mercaptoethanol.

* * * * *